US009085497B2

(12) United States Patent
Jennings

(10) Patent No.: US 9,085,497 B2
(45) Date of Patent: Jul. 21, 2015

(54) CONVERSION OF CARBON DIOXIDE TO HYDROCARBONS VIA HYDROGENATION

(71) Applicant: Air Fuel Synthesis Limited, Darlington (GB)

(72) Inventor: James Robert Jennings, Hutton Rudby (GB)

(73) Assignee: Avocet Fuel Solutions, Inc., Hockessin, DE (US)

( * ) Notice: Subject to any disclaimer, the term of this patent is extended or adjusted under 35 U.S.C. 154(b) by 0 days.

(21) Appl. No.: 14/360,420

(22) PCT Filed: Nov. 24, 2012

(86) PCT No.: PCT/EP2012/073546
§ 371 (c)(1),
(2) Date: May 23, 2014

(87) PCT Pub. No.: WO2013/076293
PCT Pub. Date: May 30, 2013

(65) Prior Publication Data
US 2014/0316016 A1    Oct. 23, 2014

(30) Foreign Application Priority Data

Nov. 25, 2011   (GB) .................................. 1120399.9

(51) Int. Cl.
*C07C 1/04* (2006.01)
*C10G 2/00* (2006.01)

(52) U.S. Cl.
CPC ................ *C07C 1/0495* (2013.01); *C10G 2/30* (2013.01); *C10G 2/32* (2013.01); *C10G 2/50* (2013.01)

(58) Field of Classification Search
CPC ............... C10G 2/32; C10G 2/33; C07C 1/04
See application file for complete search history.

(56) References Cited

U.S. PATENT DOCUMENTS

| | | | |
|---|---|---|---|
| 1,569,775 | A | 1/1926 | Mittasch et al. |
| 2,692,274 | A | 10/1954 | Kölbel et al. |
| 4,282,187 | A | 8/1981 | Corbett et al. |
| 4,327,239 | A | 4/1982 | Dorrance |
| 5,602,289 | A | 2/1997 | Van Dijk |
| 8,017,658 | B2 | 9/2011 | Tran et al. |
| 2005/0232833 | A1 | 10/2005 | Hardy et al. |
| 2006/0004111 | A1 | 1/2006 | Gagnon |
| 2006/0211777 | A1* | 9/2006 | Severinsky ................... 518/702 |
| 2008/0051478 | A1 | 2/2008 | Tran et al. |
| 2009/0320683 | A1 | 12/2009 | Hintz |
| 2010/0111783 | A1 | 5/2010 | Severinsky |
| 2010/0137457 | A1 | 6/2010 | Kaplan |
| 2014/0323600 | A1 | 10/2014 | Jennings |

FOREIGN PATENT DOCUMENTS

| | | |
|---|---|---|
| GB | 2 408 745 | 6/2005 |
| GB | 2 418 430 | 3/2006 |
| GB | 2 448 685 | 10/2008 |
| GB | 2 459 430 | 10/2009 |
| GB | 2 461 723 A | 1/2010 |
| WO | WO 93/16216 | 8/1993 |
| WO | WO 2006/036396 A2 | 4/2006 |
| WO | WO 2007/076257 A2 | 7/2007 |
| WO | WO 2008/033812 A2 | 3/2008 |
| WO | WO 2008/115933 A1 | 9/2008 |
| WO | WO 2009/048685 A1 | 4/2009 |
| WO | WO 2009/070273 A1 | 6/2009 |
| WO | WO 2009/108327 A1 | 9/2009 |
| WO | WO 2010/002469 A1 | 1/2010 |
| WO | WO 2010/112982 A1 | 10/2010 |
| WO | WO 2010/119254 A1 | 10/2010 |
| WO | WO 2013/076293 A2 | 5/2013 |
| WO | WO 2013/076293 A3 | 5/2013 |
| WO | WO 2013/076294 A1 | 5/2013 |

OTHER PUBLICATIONS

Non-Final Office Action for U.S. Appl. No. 14/360,424 "Process for the Conversion of Carbon Dioxide to Methanol", dated Nov. 6, 2014.
An, X., et al., "Methanol Synthesis from $CO_2$ Hydrogenation with a Cu/Zn/Al/Zr Figrous Catalyst", *Chinese Journal of Chemical Engineering*, 17(10): 88-94 (2009).
Arakawa, H., et al., "Selective Conversion of $CO_2$ to Methanol by Catalytic Hydrogenation Over Promoted Copper Catalyst", *Energy Convers. Mgmt*, 33(5-8), 521-528 (1992).
Chinchen, GC, et al., "The Activity of Cu—Zno—$Al_2O_3$ Methanol Synthesis Catalysts", preprints, *Am. Chem. Soc. Div. Fuel. Chem*, 29(5), 178 (1984).
Doss, B., et al., "Optimization of Methanol Synthesis from Carbon Dioxide and Hydrogen: Demonstration of a Pilot-Scale Carbon-Neutral Fuels Process", *Energy & Fuels*, 23: 4647-4650 (2009).
Hansen, J.B. and Hojlund Nielsen, P.E., "Methanol Synthesis", *Handbook of Heterogeneous Catalysis*, 2920-2949 (2008).
International Preliminary Report on Patentability/Written Opinion for International Application No. PCT/EP2012/073546, "Conversion of Carbon Dioxide to Hydrocarbons Via Hydrogenation"; Date of Mailing: May 27, 2014.
International Preliminary Report on Patentability/Written Opinion for International Application No. PCT/EP2012/073547, "Process for the Conversion of Carbon Dioxide to Methanol"; Date of Mailing: Jun. 5, 2014.

(Continued)

*Primary Examiner* — Sudhakar Katakam
(74) *Attorney, Agent, or Firm* — Hamilton, Brook, Smith & Reynolds, P.C.

(57) ABSTRACT

Carbon dioxide conversion processes are described for the conversion of carbon dioxide via hydrogenation to hydrocarbons. The process utilizes an initial feed of carbon monoxide and hydrogen converted under Fischer Tropsch conditions to hydrocarbons followed by subsequent displacement of the carbon monoxide in the reactor feed with carbon dioxide, which is then converted to carbon monoxide under reverse water gas shift conditions and the initial carbon monoxide feed being terminated once the reverse water gas shift conversion of carbon dioxide. After the optimum reaction conditions are established the feed of carbon monoxide may be withdrawn and any required carbon monoxide provided via reactor effluent recycle. The process provides for enhanced catalyst performance and life.

15 Claims, 1 Drawing Sheet

(56) References Cited

OTHER PUBLICATIONS

International Search Report for International Application No. PCT/EP2012/073546, "Conversion of Carbon Dioxide to Hydrocarbons Via Hydrogenation"; Date of Mailing: Sep. 9, 2013.

International Search Report for International Application No. PCT/EP2012/073547, "Process for the Conversion of Carbon Dioxide to Methanol"; Date of Mailing: May 7, 2013.

Lee, J.S., et al., "A Comparative Study of Methanol Synthesis from $CO_2/H_2$ and $CO/H_2$ over a $Cu/ZnO/Al_2O_3$ Catalyst", *Journal of Catalysis*, 144, 414-424 (1993).

Lee, S., et al., "Methanol Synthesis from Syngas", *Handbook of Alternative Fuel Technologies*, pp. 297-321 (2007).

Mitsui Chemicals Inc., "A New Leading Process for $CO_2$ to methanol", New Energy and Fuel, 2 pgs., Aug. 29, 2008.

Sun, J.T., et al., "Effect of Pre-Treatment on Methanol Synthesis from $CO_2/H_2$ Over $Cu/ZnO/Al_2O_3$," *Dept. of Chem. Engineering and Chem. Technology, Imperial College of Science, Technology and Medicine, London*, pp. 1128-1131 (1997).

Xin, A., et al., "Methanol Synthesis from CO2 Hydrogenation with a Cu/Zn/Al/Zr Fibrous Catalyst", *Chinese Journal of Chemical Engineering*, 17(1): 88-94 (2009).

* cited by examiner

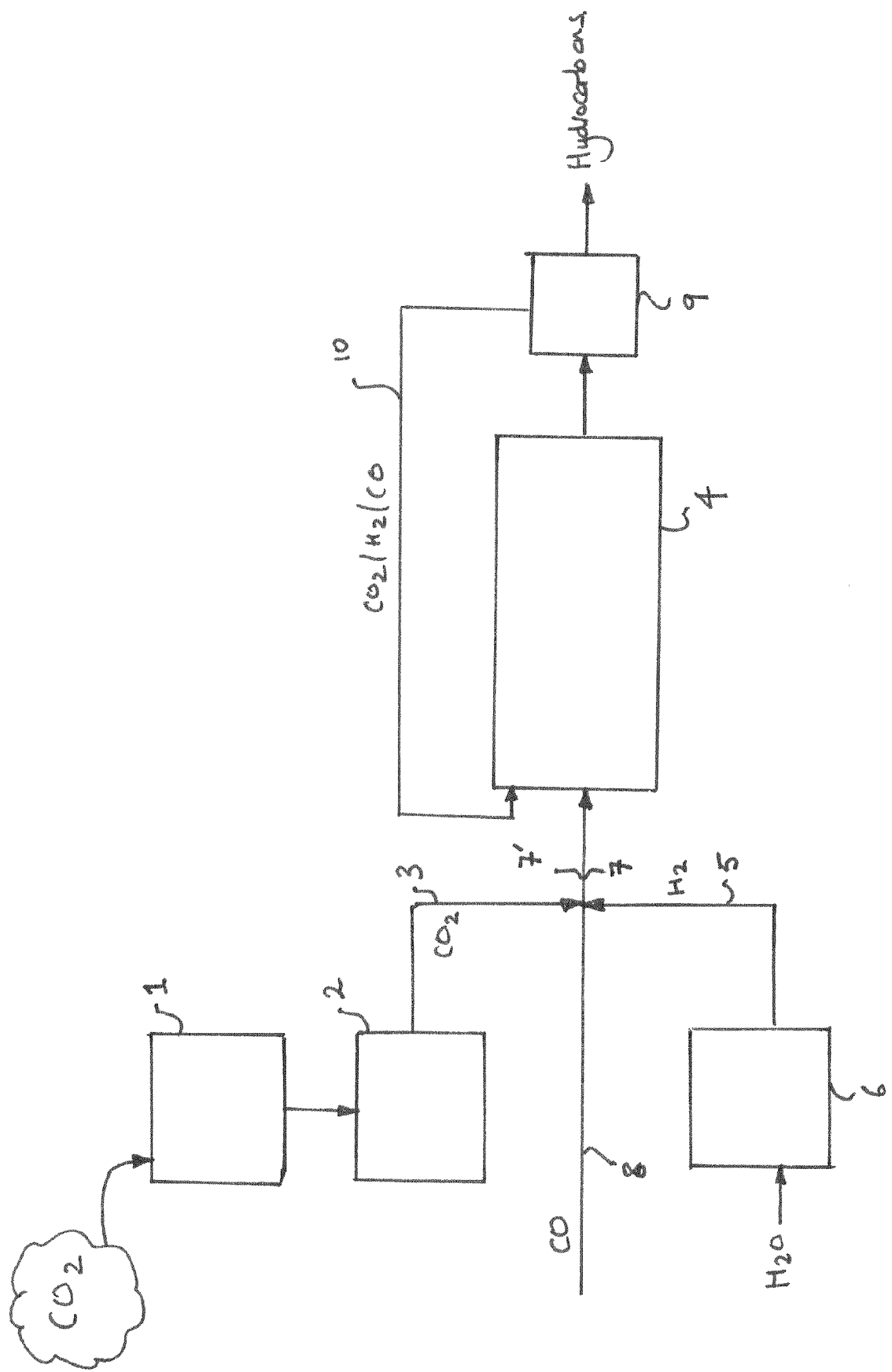

CONVERSION OF CARBON DIOXIDE TO HYDROCARBONS VIA HYDROGENATION

This application is the U.S. National Stage of International Application No. PCT/EP2012/073546, filed Nov. 24, 2012, which designates the U.S., published in English, and claims priority under 35 U.S.C. §§119 or 365(c) to Great Britain Application No. 1120399.9, filed Nov. 25, 2011.

FIELD OF INVENTION

This invention relates to a process for the conversion of carbon dioxide into hydrocarbons via the hydrogenation of carbon dioxide.

BACKGROUND ART

Due in part to global warming and climate change there is a growing interest in the use of carbon dioxide from such sources as carbon capture and storage (CCS), carbon dioxide capture from flue gases or carbon dioxide waste from industrial processes such as brewing, in the manufacture of hydrocarbons. These sources of carbon dioxide have been considered for use in combination with hydrogen obtained from water electrolysis using renewable sources of energy although in principle the hydrogen could be sourced from waste streams from conventional petrochemical processes or other sources.

One well know process for the manufacture of hydrocarbons is the Fischer-Tropsch, which converts carbon monoxide and hydrogen to hydrocarbons typically over a cobalt or iron catalyst. The usual source of carbon monoxide and hydrogen is synthesis gas or syngas.

Generally, the Fischer-Tropsch process is operated in the temperature range of 150-300° C. (302-572° F.). Higher temperatures lead to faster reactions and higher conversion rates but also tend to increase methane production. As a result, the temperature is usually maintained at the low to middle part of the range. Increasing the pressure leads to higher conversion rates and also favors formation of long-chained alkanes both of which are desirable. Typical pressures range from one to several tens of atmospheres.

A variety of synthesis gas compositions can be used. For cobalt-based catalysts the optimal $H_2$:CO ratio is around 1.8-2.1. Iron-based catalysts promote the water-gas-shift reaction and thus can tolerate significantly lower ratios. This reactivity can be important for synthesis gas derived from coal or biomass, which tend to have relatively low $H_2$:CO ratios (<1).

The conversion of carbon dioxide to hydrocarbons via hydrogenation has been know for a number of years as described for example in U.S. Pat. No. 2,692,274. In recent years there has been increasing interest given to using carbon dioxide in combination with hydrogen as a feed mixture for a Fischer-Tropsch type process with a reverse water gas shift reaction, however these emerging processes for the utilisation of carbon dioxide/hydrogen feeds are not, as yet, optimized processes and have the problems and challenges that are typically associated with such catalytic processes.

In US2005232833A1 there is described a process for producing synthetic hydrocarbons that reacts carbon dioxide, obtained from seawater of air, and hydrogen obtained from water, with a catalyst in a chemical process such as reverse water gas shift combined with Fischer Tropsch synthesis. The hydrogen is produced by nuclear reactor electricity, nuclear waste heat conversion, ocean thermal energy conversion, or any other source that is fossil fuel-free, such as wind or wave energy. The process can be either land based or sea based.

In US2008051478A1 there is described a method and apparatus of introducing hydrogen and a feed gas containing at least 50 vol % carbon dioxide into a reactor containing a Fischer-Tropsch catalyst; and heating the hydrogen and carbon dioxide to a temperature of at least about 190° C. to produce hydrocarbons in the reactor.

In WO2010002469A1 there is described a system for converting carbon dioxide into a fuel to be reburned in an industrial process. The preferred feed stocks are taken from large volume carbon dioxide producers, and municipal waste. The reaction and processes reclaim lost energy in municipal waste, and industrial exhaust gas. The system is provided with a plasma melter having a feedstock input for receiving a feed fuel, and a syngas output for producing a syngas having an $H_2$ component. Additionally, a Sabatier reactor is provided having a hydrogen input for receiving at least a portion of the $H_2$ component produced by the plasma melter, and a methane output for producing $CH_4$.

In US2010111783 there is described a process and system for producing hydrocarbon compounds or fuels that recycle products of hydrocarbon compound combustion-carbon dioxide or carbon monoxide, or both, and water. The energy for recycling is electricity derived from preferably not fossil based fuels, like from nuclear fuels or from renewable energy. The process comprises electrolysing water, and then using hydrogen to reduce externally supplied carbon dioxide to carbon monoxide, then using so produced carbon monoxide together with any externally supplied carbon monoxide and hydrogen in Fischer-Tropsch reactors, with upstream upgrading to desired specification fuels-for example, gasoline, jet fuel, kerosene, diesel fuel, and others. Energy released in some of these processes is used by other processes. Using adiabatic temperature changes and isothermal pressure changes for gas processing and separation, large amounts of required energy are internally recycled using electric and heat distribution lines. Phase conversion of working fluid is used in heat distribution lines for increased energy efficiency. The resulting use of electric energy is less than 1.4 times the amount of the high heating value of combustion of so produced hydrocarbon compounds when carbon dioxide is converted to carbon monoxide in the invention, and less than 0.84 when carbon monoxide is the source.

In GB2461723A there is described a process where carbon dioxide gas exhausted from power stations is collected by means of absorption into an absorptive fluid. The carbon dioxide is used as the carbon component for hydrocarbon or alcohol fuel. In another section, water is separated into its constituent elements, namely hydrogen and oxygen, by electrolysis. The hydrogen is combined with the carbon dioxide in an exothermic reaction to produce methanol. Methanol is a preferred automobile fuel as the pure substance or as a mixture with conventional motor fuel. If it is desired, the methanol may be converted to ethanol or conventional motor fuel. The process represents an energy conversion technology, since the carbon dioxide has no reductive (calorific) heat value, and is essentially inert.

In WO2008115933A there is described a Renewable Fischer Tropsch Synthesis (RFTS) process, which produces hydrocarbons and alcohol fuels from wind energy, waste $CO_2$ and water. The process includes (A) electrolyzing water to generate hydrogen and oxygen, (B) generating syngas in a reverse water gas shift (RWGS) reactor, (C) driving the RWGS reaction to the right by condensing water from the RWGS products and separating CO using a CuAlCl4-aromatic complexing method, (D) using a compressor with variable stator nozzles, (E) carrying out the FTS reactions in a high-temperature multi-tubular reactor, (F) separating the FTS products using high-pressure fractional condensation, (G) separating $CO_2$ from product streams for recycling through the RWGS reactor, and (H) using control methods to maintain temperatures of the reactors, electrolyzer, and condensers at optima that are functions of the flow rate. The RFTS process may also include heat engines, a refrigeration cycle utilizing compressed oxygen, and a dual-source organic Rankine cycle.

A major challenge in many catalytic processes is indentifying operating conditions, which ensure optimum utilization of the catalysts and/or process conditions. Catalysts have a useful life and must eventually be replaced or reconditioned in order to keep the process operating at the optimum conditions. The initial conditioning of the catalyst, the start-up conditions and ongoing operating conditions all have an impact on overall catalyst performance. Through any given cycle the catalyst activity will diminish and this is often compensated by changing the process to conditions that are even harsher on the catalysts resulting in accelerated catalyst deactivation. There is a typical tradeoff between the costs of catalyst replacement/reconditioning compared to the increased running costs to maintain activity.

This is a particular problem for catalysts used in processes for the conversion of carbon dioxide/hydrogen where harsh conditions may be required and catalyst life is shortened as a consequence.

DISCLOSURE OF THE INVENTION

The present invention is concerned with processes for the conversion of carbon dioxide to hydrocarbons, which utilize carbon monoxide in the process to improve the initial or start-up operating conditions of the process and the subsequent life and activity of the catalysts used.

With reference to the present invention it has been found that if a certain sequence of initial process steps are utilized in a process for the conversion of carbon dioxide to hydrocarbons in the presence of hydrogen, which utilizes a temporary initial carbon monoxide feed to the reactor, then this allows the subsequent introduction of carbon dioxide to be made under conditions which have a positive impact on operating conditions and catalyst life.

In the process of the present invention the reaction effluent may be processed to enable a mixture of un-reacted hydrogen, carbon dioxide and carbon monoxide, to be separated from the hydrocarbon and any oxygenated hydrocarbon products and to be recycled into the reactor.

Once carbon dioxide has been introduced to the reactor the carbon monoxide feed to the reactor is reduced as the carbon monoxide for the FT reaction is generated in-situ within the reactor due to the reverse water gas shift reaction and will also contain any un-reacted and recycled carbon monoxide.

In essence the initial carbon monoxide/hydrogen feed is introduced to enable the conversion to hydrocarbons to proceed under standard Fischer Tropsch conditions and then carbon dioxide is introduced to the feed with the simultaneous reduction and removal of the initially added carbon monoxide. At steady state, the required carbon monoxide for the Fischer Tropsch reaction is derived only from carbon dioxide through the reverse water gas shift reaction within the reactor. At this point the only feeds into the reactor are carbon dioxide (preferably from carbon dioxide capture from the atmosphere), hydrogen (preferably from the electrolysis of water using carbon neutral electricity) and reactor recycle, which has been separated from the hydrocarbon and any oxygenated hydrocarbon products.

Thus the present invention provides a process for the conversion of carbon dioxide to hydrocarbons via hydrogenation, which process comprises:
A) initial introduction of a first reactor feed comprising carbon monoxide and hydrogen to a reactor operated under Fischer Tropsch conditions to produce hydrocarbons,
B) subsequent introduction of carbon dioxide to the reactor with an equivalent reduction of introduced carbon monoxide from the initial reactor feed, with the reactor conditions set to maximize the conversion of carbon dioxide to carbon monoxide within the reactor via the reverse water gas shift reaction, and
C) maintaining operation of the reactor without any introduced carbon monoxide.

In a further embodiment the process comprises separation of non converted reactants from the reactor effluent for recycle to the reactor. In a preferred embodiment the non converted reactants comprises one or more of carbon dioxide, hydrogen and carbon monoxide. Thus any carbon monoxide formed in the reactor may be added, through recycle, to the incoming carbon dioxide/hydrogen feed and thus contributing to the reduction of the introduced carbon monoxide to the reactor feed. The composition of the recycle becomes the combination of non-reacted carbon dioxide, carbon monoxide and hydrogen as mixture or they may be recycled as individual feeds to the corresponding feed to the reactor or they may be introduced to the reactor as binary mixtures with or without supplemental introduction of fresh feed of each component of the mixture.

It is preferred that the carbon dioxide is provided from recovery of carbon dioxide from the atmosphere, the oceans and/or the effluent streams of industrial processes. There are various processes through which this may be achieved including adsorption such as amine based adsorption, high pressure absorption processes, membrane processes and cryogenic processes.

One preferred process for carbon dioxide capture and release is a two stage process where carbon dioxide is scrubbed from the air or stream comprising carbon dioxide with a scrubber preferably using sodium hydroxide. Examples of technology that may be used in this stage of the process are described in WO2010119254A1, WO2009070273A1, WO2006036396A2 and US2009320683A1. Other suitable processes for carbon dioxide recovery include high temperature carbonate/bicarbonate processes.

This first stage produces a sodium carbonate/sodium hydroxide mixture, which may be fed into an electrolysis cell where the feed is electrolysed to produce carbon dioxide, which may be fed to the reactor or intermediate storage. In a preferred embodiment the electricity for the electrolysis and the scrubbing stages is sourced from renewable source of electricity and most preferably carbon neutral sources of electricity. A suitable electrolysis process for the release of carbon dioxide from such mixtures is as described in published international patent application WO9316216A1, the whole contents of which are hereby incorporated by reference.

It is preferred that the hydrogen is provided from the electrolysis of water, preferably utilizing carbon neutral or renewable sources of electricity. One such source could be nuclear power.

Any water generated in the process may be recycled for electrolysis to hydrogen for use in the process.

It is preferred that the hydrogenation reaction is undertaken at 400° C. or less, preferably 350° C. or less and most preferably 320° C. or less. A preferred reaction temperature is between 250 and 320° C.

It is preferred that the hydrogenation reaction is undertaken at a pressures typically utilized for conversion of carbon monoxide/hydrogen mixtures to hydrocarbons under Fischer Tropsch conditions.

In the early stages of the reaction the hydrogen and carbon monoxide may be introduced to the reactor in proportions typically used in a Fischer Tropsch process.

The carbon dioxide may be introduced to the reactor feed of carbon monoxide and hydrogen at an initial low level and is increased as the added carbon monoxide feed is reduced to zero and is then maintained at a level in proportion to hydrogen required to allow the catalyst to function at an acceptable rate and at an acceptable temperature under reverse water gas shift conditions to produce hydrocarbons.

In the process of the present invention the catalyst may be any suitable catalyst for the hydrogenation of carbon monoxide to hydrocarbons. Examples of suitable catalysts include conventional Fischer Tropsch catalysts such as cobalt or iron based catalysts. Preferably the catalysts used are those that in addition to catalyzing the conversion of carbon monoxide and hydrogen to hydrocarbons are also able to catalyze the reverse water gas shift reaction.

Examples of such catalysts are as described in WO2007076257A2, the whole contents of which are hereby incorporated by reference.

A present invention is exemplified and will be better understood upon reference to the following detailed description when read in conjunction with the accompanying drawing and in which:

FIG. 1 is a schematic view of a preferred process according to the present invention.

BRIEF DESCRIPTION OF THE DRAWINGS

With reference to FIG. 1, there is exemplified a process for the conversion of carbon dioxide to hydrocarbons via hydrogenation. The carbon dioxide is captured from the atmosphere via the scrubber unit (1), which produces a sodium carbonate/sodium hydroxide mixture, which passes to an electrolyser unit (2), which utilises renewable and preferably carbon neutral electricity to electrolyse the sodium carbonate/sodium hydroxide mixture to produce carbon dioxide feed (3). The hydrogen required for the process and supplied through feed (5), which is combined with the carbon dioxide feed (3), is produced by the electrolysis of water in electrolysis unit (6), which utilises renewable and preferably carbon neutral electricity for the electrolysis. The carbon dioxide/hydrogen mixed feed (7') when formed is passed into the reactor (4) for conversion to hydrocarbons. At start-up of the process the carbon dioxide feed (3) is turned off and a carbon monoxide feed (8) is combined with the hydrogen feed (5) to produce a carbon monoxide/hydrogen feed (7) into the reactor (4). This initial carbon monoxide/hydrogen feed (7) is converted in the reactor (4) under Fischer Tropsch conditions to hydrocarbons. As the reaction is initiated, preferably with the use of catalysts that promote the reverse water gas shift reaction (RWGS), the carbon dioxide feed (3) is gradually introduced to feed (7) and the carbon monoxide feed (8) is proportionally reduced. There will also be a need to adjust the carbon:hydrogen ratio as conversion of carbon dioxide to hydrocarbons requires more hydrogen than carbon monoxide, unless the initial feed is hydrogen rich. During this transition the carbon dioxide entering the reactor (4) is converted under RWGS conditions to carbon monoxide, which is then partially converted to hydrocarbons under Fischer Tropsch conditions, the remainder going into the recycle gas. Eventually the carbon monoxide feed (3) is completely displaced from the feed (7) by the carbon dioxide feed (3) and we in effect have a new feed (7') of carbon dioxide and hydrogen being passed into the reactor. This feed is converted under RWGS and Fischer Tropsch conditions within the reactor (4) into hydrocarbons and carbon monoxide. Any un-reacted carbon dioxide, carbon monoxide and/or hydrogen present in the output from the reactor (4) may be separated in separator (9) from the hydrocarbons produced and recycled through feed (10) into the reactor (4).

The invention claimed is:

1. A process for the conversion of carbon monoxide and carbon dioxide to hydrocarbons via hydrogenation, which process comprises:
   a) initially introducing a reactor feed comprising carbon monoxide and hydrogen to a reactor operated under Fischer Tropsch conditions for a period of time sufficient to initiate the conversion of carbon monoxide to produce hydrocarbons;
   b) subsequently introducing carbon dioxide into the reactor while reducing the amount of carbon monoxide initially introduced into the reactor feed according to step (a), under conditions to maximize the conversion of carbon dioxide to carbon monoxide within the reactor via the reverse water gas shift reaction; and
   c) maintaining operation of the reactor to produce hydrocarbons using the carbon monoxide generated in step (b), without continued introduction of carbon monoxide according to step (a) via the initial reactor feed.

2. A process as claimed in claim 1, which further comprises separation of non converted reactants from the reactor effluent for recycle to the reactor.

3. A process as claimed in claim 2, wherein the non-converted reactants comprises one or more of carbon dioxide, hydrogen and carbon monoxide.

4. A process as claimed in claim 2, wherein the carbon monoxide in the initial reactor feed is reduced or terminated after recycle of non converted reactants, as the concentration of carbon monoxide produced in the reactor becomes sufficient to sustain reaction.

5. A process as claimed in claim 2, wherein the recycle comprises a combination of non-reacted carbon dioxide, carbon monoxide and hydrogen as a mixture.

6. A process as claimed in claim 2, wherein the recycled reactants are recycled as individual feeds to the corresponding feed to the reactor.

7. A process as claimed in claim 2, wherein the recycled reactants are recycled as binary mixtures with or without supplemental introduction of fresh feed of each component of the mixture.

8. A process as claimed in claim 1 wherein the carbon dioxide feed is provided from recovery of carbon dioxide from a carbon dioxide source such as the atmosphere, the oceans and/or the effluent streams of industrial processes.

9. A process as claimed in claim 8 wherein the feed is provided via a two stage process comprising caustic scrubbing of carbon dioxide form the carbon dioxide source followed by electrolysis of the caustic/sodium carbonate mixture to release carbon dioxide.

10. A process as claimed in claim 1 wherein the hydrogen is provided from the electrolysis of water.

11. A process as claimed in claim 10, wherein the water electrolysis is carried out using a carbon neutral or renewable sources of electricity.

12. A process as claimed in claim 1 wherein the hydrogenation reaction is undertaken at 400 ° C. or less.

13. A process as claimed in claim 1 wherein the hydrogenation reaction is undertaken at 350 ° C. or less.

14. A process as claimed in claim 1 wherein the hydrogenation reaction is undertaken at 320 ° C. or less.

15. A process as claimed in claim 1 wherein the hydrogenation reaction is undertaken between 250 and 320 ° C.

* * * * *